United States Patent
Golz-Berner et al.

(10) Patent No.: US 7,303,774 B2
(45) Date of Patent: Dec. 4, 2007

(54) RELAX COSMETIC HAVING A TEMPERATURE EFFECT

(75) Inventors: Karin Golz-Berner, Monaco (MC); Leonhard Zastrow, Monaco (MC)

(73) Assignee: Coty B.V. (NL)

( * ) Notice: Subject to any disclaimer, the term of this patent is extended or adjusted under 35 U.S.C. 154(b) by 0 days.

(21) Appl. No.: 10/741,335

(22) Filed: Dec. 19, 2003

(65) Prior Publication Data
US 2004/0146483 A1     Jul. 29, 2004

(30) Foreign Application Priority Data
Dec. 19, 2002   (DE) ................... 102 61 815

(51) Int. Cl.
*A61K 36/53* (2006.01)
*A61K 36/00* (2006.01)

(52) U.S. Cl. ............... 424/747; 424/725; 424/776; 424/778

(58) Field of Classification Search ........... 424/747, 424/778
See application file for complete search history.

(56) References Cited

U.S. PATENT DOCUMENTS 4,880,621 A * 11/1989 Grollier et al. ............... 424/74
5,972,322 A * 10/1999 Rath et al. ............... 424/70.11
6,551,606 B1    4/2003 Golz-Berner et al.
2003/0125303 A1* 7/2003 Kucharchuk ............... 514/62
2003/0190300 A1* 10/2003 Scancarella et al. ..... 424/70.12
2007/0134189 A1* 6/2007 Golz-Berner et al. .... 424/70.14

FOREIGN PATENT DOCUMENTS

CA        2327003 A1 *  5/2002

OTHER PUBLICATIONS

Internet website http://web.archive.org/web/20020621201107/http://www.wholehealthmd.com/refshelf/substances_view/1,1525,812,00.html (9 pages total).*
Internet website http://web.archive.org/web/20021119010652/http://www.ibiblio.org/pfaf/cgi-bin/arr_html?Papaver+rhoeas &CAN=COMIND (3 pages total).*
Lexikon der kosmetischen Praxis, Wien 1936, pp. 369-370.
Springer-Lexikon Kosmetik u. Koerperpflege, Berlin 2001, pp. 262-265.

* cited by examiner

*Primary Examiner*—Christopher R. Tate
(74) *Attorney, Agent, or Firm*—Stephen Pendorf; Akerman Senterfitt

(57) ABSTRACT

The present invention relates to new cosmetic relax preparations bringing about changing temperature effects on the skin. Said cosmetic contains 0.1-10% by weight of an extract from Papaveraceae and 0.1-10% by weight of an extract from the overground parts of Menthae, along with 80-99.8% by weight of cosmetic auxiliaries, carrier substances, active agents or mixtures thereof.

9 Claims, No Drawings

RELAX COSMETIC HAVING A TEMPERATURE EFFECT

FIELD OF THE INVENTION

The present invention relates to new cosmetic relax preparations bringing about changing temperature effects on the skin.

DESCRIPTION OF THE RELATED ART

It has long been known to incorporate peppermint (Menthae) extracts into sweets, cigarettes, ice cream and liquors as well as into cosmetic preparations, e.g. mouthcare products, toilet products and perfumes. Peppermint oil is mainly used to treat disorders of the upper respiratory tract, skin irritations, neuralgic pain and digestive trouble. From a cosmetic point of view, the mint's cooling and refreshing effects as well as its antibacterial action are of particular interest.

Poppy (Papaveraceae) has become known in medicine due to its alkaloid content (morphine, codeine); in addition, its seeds are used in Ayurvedic medicine to treat digestive trouble. WO 00/76458 discloses a cosmetic product containing enzymes which, inter alia, contains the plant milk-water of poppy along with coconut milk and rice hull oil and/or rice germ oil.

SUMMARY OF THE INVENTION

The object of the invention is to provide a new cosmetic product having a relaxing and a temperature effect.

The cosmetic according to the invention contains 0.1-10% by weight of an extract from Papaveraceae and 0.1-10% by weight of an extract from the overground parts of Menthae, along with 80-99.8% by weight of cosmetic auxiliaries, carrier substances, active agents or mixtures thereof, all percentages being relative to the cosmetic's total weight.

The Papaveraceae extracts may be obtained from the plants' petals and seed capsules. Extracts obtained from the petals are preferred. Preferred poppy species are *Papaver rhoeas* and *Papaver somniferum*, of which *Papaver rhoeas* is particularly preferred.

The Menthae extracts may be obtained from the plants' leaves and stems. Extracts obtained from the leaves are preferred. Preferred mint species are *Mentha aquatica, Mentha arvensis* and *Mentha piperita.*

The extractants which may be used for the invention include water, lower alcohols, e.g. ethanol, or polyvalent alcohols, e.g. propylene glycol, or mixtures of propylene glycol and glycerine. Perfume preparations are preferably produced using alcoholic extracts.

In a special embodiment of the invention, the Papaveraceae and Menthae extracts are alcoholic extracts and the cosmetic is provided in the form of a perfume in which the active agents are contained in amounts ranging between 2.5 and 10% by weight each.

Another preferred embodiment of the invention is a relax cosmetic in which the Papaveraceae and Menthae extracts are provided mixed with a self-emulsifying silicone gel and wherein said extracts contained in the self-emulsifying silicone gel may moreover be provided in an encapsulated form. However, said extracts may also be incorporated into the gel structure in a non-encapsulated condition.

It has been found that the cosmetic preparation according to the invention brings about a noticeable cooling effect on the skin which after a short time (a few seconds, depending on the skin type) is followed by a heat effect of similar intensity. The heat effect replacing the initial cooling effect passes rather slowly and brings about a clearly relaxing effect on the skin, thus achieving an overall relaxing effect on the user. If the active agents used according to the invention, i.e. mint and poppy, are provided in the special combination with a self-emulsifying silicone gel, their total activity is increased even further and a skin-firming effect can be observed. The relaxing effect on the skin achieved after mixing said active agents with silicone gel in particular clearly exceeds the effect brought about by the individual components.

Particularly pronounced effects on the skin are achieved if the cosmetic which is no perfume contains mint in an amount ranging between 1.5 and 6% by weight and poppy in an amount ranging between 1 and 4% by weight, both percentages referring to the extracts' dry substance.

The cosmetic according to the invention further contains cosmetic auxiliaries and carrier substances as they are commonly used in such preparations, e.g. water, preservatives, colourants, pigments having a colouring effect, thickeners, fragrances, alcohols, polyols, esters, electrolytes, gel-forming agents, polar and non-polar oils, polymers, copolymers, emulsifiers, waxes, stabilizers and emollients.

The oils used for the invention may be commonly used cosmetic oils, e.g. mineral oil; silicone oils; hydrogenated polyisobutene; synthetic squalane or squalane made from natural products; cosmetic esters or ethers, which may be branched or unbranched, saturated or unsaturated; vegetable oils; or mixtures of two or more thereof.

Silicone oils are particularly suitable. Water/silicone oil (W/S) emulsions are preferably produced using self-emulsifying silicone gels, e.g. KSG-21® or KSG-210® (manufactured by Shin-Etsu Silicones of America, Akron, Ohio, USA).

A plurality of compounds may normally be used as emollients, e.g. stearyl alcohol, glyceryl monoricinoleate, glyceryl monostearate, propane-1,2-diol, butane-1,3-diol, cetyl alcohol, isopropyl isostearate, stearic acid, isobutyl palmitate, isopropyl myristate, isopropyl palmitate, oleyl alcohol, isopropyl laurate, decyl oleate, octadecane-2-ol, iso-cetyl alcohol, cetyl palmitate, silicone oils such as dimethyl polysiloxane, polyethylene glycol, lanolin, cocoa butter, vegetable oils such as maize oil, cotton seed oil and olive oil, mineral oils, butyl myristate, palmitic acid, etc.

Other active agents may also be contained, e.g. inorganic and organic sunscreens, scavengers, moisturizing substances, vitamins, enzymes, plant-based active agents, anti-oxidants, anti-inflammatory natural active agents, asymmetric lamellar aggregates loaded with oxygen according to WO 94/00109, decomposition products of yeasts or plant-based substances obtained by means of a gentle ultrasonic decomposition process according to WO 94/13783, kaolin and kaolin modified with $SiO_2$ according to WO 94/17588.

In addition, the cosmetic according to the invention may contain an active formulation having a high radical protection factor and containing a product obtained by extracting the bark of *Quebracho blanco* and subsequent enzymatic hydrolysis, which product contains at least 90% by weight pro-anthocyanidine oligomers and max. 10% by weight gallic acid and is contained in micro-capsules, along with a silkworm extract obtained by extraction, which extract contains the peptide cecropine, amino acids and a vitamin mixture, and a non-ionic, cationic or anionic hydro-gel or mixture of hydrogels and one or more phospholipid(s) and water according to WO 99/66881.

The antioxidants and scavengers mentioned above include vitamins such as vitamin C and derivatives thereof, e.g. ascorbyl acetate, ascorbyl phosphate and ascorbyl palmitate; vitamin A and derivatives thereof; folic acid and derivatives thereof; vitamin E and derivatives thereof, e.g. tocopheryl acetate; flavones or flavonoids; amino acids, e.g. histidine, glycine, tyrosine, tryptophan and derivatives thereof; carotenoids and carotenes, e.g. α-carotene, β-carotene; uric acid and derivatives thereof; and α-hydroxy acids, e.g. citric acid, lactic acid, malic acid.

It is particularly advantageous that a mixture of enzymes and vitamins be used which is a decomposition product obtained by subjecting a yeast to an ultrasonic process, which decomposition product contains SOD, protease, vitamin $B_2$, vitamin $B_6$, vitamin $B_{12}$, vitamin $D_2$ and vitamin E. Said product preferably contains at least 150 U/ml SOD, protease and vitamins B and D, the ratio of SOD to protease expressed in international units ranging at least between 3:1 and 8:1.

The cosmetic according to the invention may further contain polyols. Polyols include e.g. propylene glycol, dipropylene glycol, ethylene glycol, isoprene glycol, glycerine, butylene glycol, sorbitol and mixtures thereof. The polyol makes up 0.1-40% by weight, preferably approx. 5-20% by weight, of the composition.

Moisturizing substances which may be used include glycerine, butylene glycol, propylene glycol and mixtures thereof.

The cosmetic active agents, particularly mint and poppy, may be encapsulated in usual liposomes which serve as a transport system. Liposomes are completely closed lipid bilayer membranes enclosing an aqueous volume. Liposomes can be unilamellar vesicles (i.e. having a single membrane bilayer) or multilamellar vesicles (i.e. onion-like structures characterized by several membrane bilayers each of which is separated from the next one by an aqueous layer). The production of liposomes from saturated and unsaturated lipids has been described in a large number of patents, as well as their use as a transport system. The active agents may be encapsulated therein in a manner known per se. Such liposomes are mostly made from phospholipids. Alternatively, the active agents according to the invention may also be encapsulated in alginates or other gel-like structures.

The cosmetic composition according to the invention may be used e.g. in the form of gels, after-sun products, day creams, night creams, masks, body lotions, cleansing milk, shower gels, shower oils, bath oils, eau de toilette, eau de parfum, perfumes, sun products for use in winter and in decorative cosmetic products such as deo sticks, perfume sticks, lipsticks and compact products, e.g. rouge, foundations, make-up, etc.

The invention further relates to a method for producing a relax cosmetic comprising the steps of making extracts of Papaveraceae and Menthae into a powder whose particle size ranges between 0.1 and 25 μm, dissolving said powder in a little water and mixing it with a self-emulsifying silicone gel at a temperature of 60-65° C. for 5-20 minutes and at a rate of 400-1,000 rpm, preferably 600-1,000 rpm. In this way, a gel is obtained in which the active agents' effective structure is preserved and which has a noticeable effect on the skin, even if the active agents are contained only in small amounts ranging between 0.1 and 1.5% by weight.

The invention will hereinafter be explained in more detail by means of examples. All quantities are in percent by weight unless indicated otherwise.

EXAMPLE 1

Silicone/Water Gel Cream

| Phase A | |
|---|---|
| Water | q.s. ad 100 |
| Glycerine | 1.0 |
| Disodium Hydrogenphosphate | 0.5 |
| Sodium Chloride | 1.5 |
| Phase B | |
| Silicone | 2.0 |
| Silicone Gel KSG-210 ® | 3.0 |
| Phase C | |
| Ethanol | 10 |
| Phase D | |
| *Mentha piperita* Extract (aqueous) | 3.0 |
| *Papaver rhoeas* Extract (aqueous) | 3.0 |
| Phase E | |
| Perfume | 0.2 |
| Preservative | 0.5 |

Phase A and Phase B are prepared separately at a temperature of max. 65° C. and max. 60° C. respectively and are then mixed with one another while stirring and the mixture is stirred for another 10 minutes at 800-1,000 rpm. The mixture is cooled down while stirring slowly, Phase C is added at 30° C. and the mixture is cooled down to 25° C. while stirring.

Phase D is prepared by adding the dry powdery extracts to approx. 10% of the total amount of water while stirring at 50-100 rpm and added to the mixture while stirring. Finally, Phase E is added and the overall mixture is stirred for 10 minutes at approx. 1,000 rpm.

EXAMPLE 2

Perfume

| Water | 1.5 |
|---|---|
| Perfume Oil | 13 |
| Ethanol | q.s. ad 100 |
| *Mentha arvensis* Extract (alcohol.) | 3.0 |
| *Papaver rhoeas* Extract (alcohol.) | 3.0 |

The components are mixed with one another in the order indicated above.

EXAMPLE 3

Sun Product for Winter Sun, SPF 15

| Phase A | |
|---|---|
| Water | q.s. ad 100 |
| Glycerine | 1.0 |
| Disodium Hydrogenphosphate | 0.5 |
| Sodium Chloride | 1.5 |
| Phase B | |

-continued

| | |
|---|---|
| Cyclohexasiloxane | 5 |
| Uvinul MC 80 | 5 |
| Parsol 1768 | 3 |
| Escalol 587 | 5 |
| Silicone Gel KSG-210 ® | 3.0 |
| Phase C | |
| Ethanol | 2 |
| Mentha piperita Extract and Papaver rhoeas Extract encapsulated in liposomes (1:1) | 5.0 |
| Perfume Oil | 0.5 |
| Preservative | 0.5 |
| Active complex having a radical protection factor according to WO 99/66881, Example 1 | 10 |

Phase A and Phase B are prepared separately and then mixed with one another, the mixture is cooled down to 30° C. while stirring and Phase C is added. The mixture is stirred for 20 minutes at approx. 1,000 rpm.

EXAMPLE 4

After-Sun Lotion

| | |
|---|---|
| Phase A | |
| Water | q.s. ad 100 |
| Glycerine | 1.0 |
| Disodium Hydrogenphosphate | 0.5 |
| Sodium Chloride | 0.8 |
| Phase B | |
| Silicone | 1 |
| Silicone Gel KSG-210 ® | 2 |
| Phase C | |
| Mentha aquatica Extract (alcohol.) | 2.0 |
| Papaver somniferum Extract (alcohol.) | 2.0 |
| Perfume Oil | 0.5 |
| Preservative | 0.5 |
| Processing is done as in Example 1. | |

The invention claimed is:

1. A relax cosmetic having a temperature effect which comprises
    (a) 0.-10% by weight of an extract from petals, seed capsules or a mixture thereof of Papaveraceae selected from the group consisting of *Papaver rhoeas, Papaver somniferum* and combinations thereof, and
    (b) 0.1-10% by weight of an extract from the overground parts of Menthae selected from the group consisting of *Mentha aquatica, Mentha arrensis, Mentha piperita* and combinations thereof, along with
    (c) 88-99.8% by weight of cosmetic auxiliaries, carrier substances, topically effective active agents other than (a) and (b), or mixtures thereof, all percentages being relative to the cosmetic's total weight wherein said relax cosmetic is formulated to bring about a noticeable cooling effect when applied to the skin which after a short time is followed by a heat effect of similar intensity to bring about a relaxing effect on the skin.

2. A relax cosmetic according to claim 1, wherein the Papaveraceae extract is an aqueous extract obtained from petals.

3. A relax cosmetic according to claim 1, wherein the Papaveraceae and Menthae extracts are alcoholic extracts and the cosmetic is provided in the form of a perfume in which the active agents are contained in amounts ranging between 2.5 and 10% by weight each.

4. A relax cosmetic as in claim 1, wherein said extracts (a) and (b) are aqueous or alcoholic extracts.

5. A relax cosmetic as in claim 1 wherein said extracts (a) and (b) are obtained using an extractant selected from the group consisting of water, lower alcohols, polyvalent alcohols, or mixtures thereof.

6. A relax cosmetic according to claim 1, wherein the Papaveraceae and Menthae extracts are alcoholic extracts and the cosmetic is provided in the form of a perfume in which the active agents are contained in amounts ranging between 2.5 and 10% by weight each.

7. A relax cosmetic having a temperature effect which comprises
    (a) 0.1 -10% by weight of an extract from the petals, seed capsules or a mixture thereof of Papaveraceae selected from the group consisting of *Papaver rhoeas, Papaver somniferum* and combinations thereof, and
    (b) 0.1-10% by weight of an extract from the overground parts of Menthae selected from the group consisting of *Mentha aquatica, Mentha arrensis, Mentha piperita* and combinations thereof, along with
    (c) 88-99.8% by weight of cosmetic auxiliaries, carrier substances, topically effective active agents other than (a) and (b), or mixtures thereof, all percentages being relative to the cosmetics total weight wherein said relax cosmetic is formulated to bring about a noticeable cooling effect when applied to the skin which after a short time is followed by a heat effect of similar intensity to bring about a relaxing effect on the skin, and wherein the Papaveraceae and Menthae extracts are provided mixed with a self-emulsifying silicone gel.

8. A relax cosmetic according to claim 7, wherein said extracts contained in the self-emulsifying silicone gel are provided in an encapsulated form.

9. A relax cosmetic according to claim 7, wherein said extracts contained in the self-emulsifying silicone gel are provided in an encapsulated form.

* * * * *